United States Patent [19]

Peralta

[11] Patent Number: 4,806,099
[45] Date of Patent: Feb. 21, 1989

[54] FLUIDIC CONTROL ASSEMBLY FOR DENTAL TOOLS

[76] Inventor: Michael A. Peralta, 3500 Washington St., Apt. No. A-212, Hollywood, Fla. 33021

[21] Appl. No.: 115,198

[22] Filed: Nov. 2, 1987

[51] Int. Cl.⁴ .............................................. A61C 19/02
[52] U.S. Cl. .................................................. 433/28
[58] Field of Search ..................... 137/872; 433/28, 27

[56] References Cited

U.S. PATENT DOCUMENTS

| | | | |
|---|---|---|---|
| 3,638,310 | 1/1972 | Austin | 433/28 |
| 4,069,587 | 1/1978 | Peralta | 433/28 |
| 4,117,861 | 10/1978 | Betush | 433/28 |
| 4,230,452 | 10/1980 | Austin | 433/28 |

Primary Examiner—Robert Peshock

[57] ABSTRACT

A fluidic control assembly for controlling the supply of drive air and/or water to a tool such as a dental handpiece in response to its presence or absence in a hanger in which it is removably stored. The assembly comprises a primary fluidic control and a secondary control, with the primary fluidic control having a control valve which directs the flow of drive air from a source of supply through a primary chamber to a main outlet coupled to the handpiece. The control valve extends into a secondary chamber having means for operating the control valve in response to a predetermined pressure level in the secondary chamber. The secondary chamber communicates with the secondary control, which is integrated in the hanger for sensing the presence or absence of the tool in the hanger. The secondary control causes a build-up of pressure in the secondary chamber when the tool is absent from the hanger and causes the pressure in the secondary chamber to drop below the predetermined level when the tool is present.

8 Claims, 4 Drawing Sheets 4,806,099

FLUIDIC CONTROL ASSEMBLY FOR DENTAL TOOLS

BACKGROUND OF THE INVENTION

1. Field of the Invention

This invention relates to a fluidic control assembly for controlling the delivery of air and/or water to dental equipment and, more particularly, to a fluidic control assembly for a dental tool such as a handpiece.

2. Description of the Prior Art

Conventional dental drills are operated at relatively high speeds by an air turbine driven from a source of air at a regulated pressure. High speed dental drills usually also have provision for discharging water as a stream, or jet in direct proximity to the drill. Likewise air may be delivered either with or without the drill itself being turned on. Water and air are supplied to the drill from separate water and air supply source in the dental office.

It is typical for the supply of air and/or water to be operated from a foot switch under the control of the dentist. In addition to the foot switch, a control assembly is used to automatically control the supply of drive air to the dental drill and to discharge a stream of water into the oral cavity. The control assembly is generally designed to operate in response to the removal of the tool or handpiece from its cradle. Prior art control assemblies are designed to use pneumatic valves in combination With electrical and/or hydraulic controls to form a complex and expensive control unit, which is difficult to install and generally requires a substantial amount of expertise to repair and maintain.

A more recent control arrangement developed by applicant uses a modular fluidic block design as shown and described in U.S. Pat. No. 4,459,106. Although the fluidic block forms a compact control unit, it is operationally dependent upon the accuracy in alignment between a source of compressed air and a sensing chamber for detecting the presence or absence of the handpiece in its hanger. A laminar flow of air must bridge an air gap and strike a diaphragm in the sensing chamber When the tool is removed from the hanger. The tool otherwise fills the air gap, blocking the air flow. Accordingly, the accuracy in alignment between the source of compressed air and the sensing chamber is critical to the operation of the control unit and requires each unit to be factory tailored and tested. Moreover, the operation between the control unit, the handpiece, and the valve diaphragm in the sensing chamber are so mechanically interrelated that specialized personnel are necessary to undertake the installation of the control unit in the dental office. In addition, the control unit is part of the hanger assembly and cannot be separated for repair. Accordingly all repair must be done directly in the dental office or the entire assembly, including the handpiece and hanger, must be removed from the dental office.

A substantial need has developed for a more simplified control unit, and preferably of miniature size which requires no special training to install, is easy to maintain, and may be physically independent of the hanger assembly so that the control unit can be repaired simply by replacement with a substitute unit While the inoperative unit is returned to the factory.

SUMMARY OF THE INVENTION

It is the principal object of the present invention to provide a miniature size fluidic control assembly in the form of a cassette for controlling the supply of air and water to a dental tool which is inexpensive to manufacture, easy to install and requires no maintenance.

It is a further object of the present invention to provide an inexpensive control assembly for controlling the supply of air and water to a dental tool which incorporates a primary fluidic control unit for providing drive air and/or water to the dental tool and a secondary control responsive to the presence and/or withdrawal of the dental tool from its hanger to actuate the primary unit.

It is an even further object of the present invention to provide a fluidic control assembly for supplying air and/or water to a dental tool which includes a manual bypass in said secondary control for permitting a tool to be removed from its hanger for replacement of a dental burr without causing drive air and/or water to be supplied.

These and other objects are attained in accordance with the fluidic control assembly of the present invention which includes:

a primary fluidic control unit for supplying drive air and/or water to a dental tool adapted to be removably stored in a hanger and a secondary pneumatic control for causing the primary control to either supply or interrupt drive air to such dental tool in response to the presence or absence of the dental tool from its hanger; wherein the primary fluidic control unit is formed from a modular body comprising:

- a control chamber having a main inlet and a main outlet;
- means for introducing drive air through said main inlet and into said control;
- a control valve for directing drive air from said chamber into said main outlet when said valve is open;
- a secondary chamber;
- means for bleeding air from said control chamber into said secondary chamber;
- means in said secondary chamber for opening said control valve When the pressure in said secondary chamber builds up to above a predetermined level;
- means for discharging air from said secondary chamber to maintain the pressure therein below said predetermined level; and
- means for coupling said secondary chamber to said secondary control wherein said secondary control includes means for blocking the discharge of air from said secondary chamber in response to the absence of said dental tool from the hanger.

BRIEF DESCRIPTION OF THE DRAWINGS

Other objects and advantages of the present invention will become apparent from the following detailed description of the invention, when read in conjunction with the accompanying drawings of which.

DESCRIPTION OF THE PREFERRED EMBODIMENT

Figure 1:
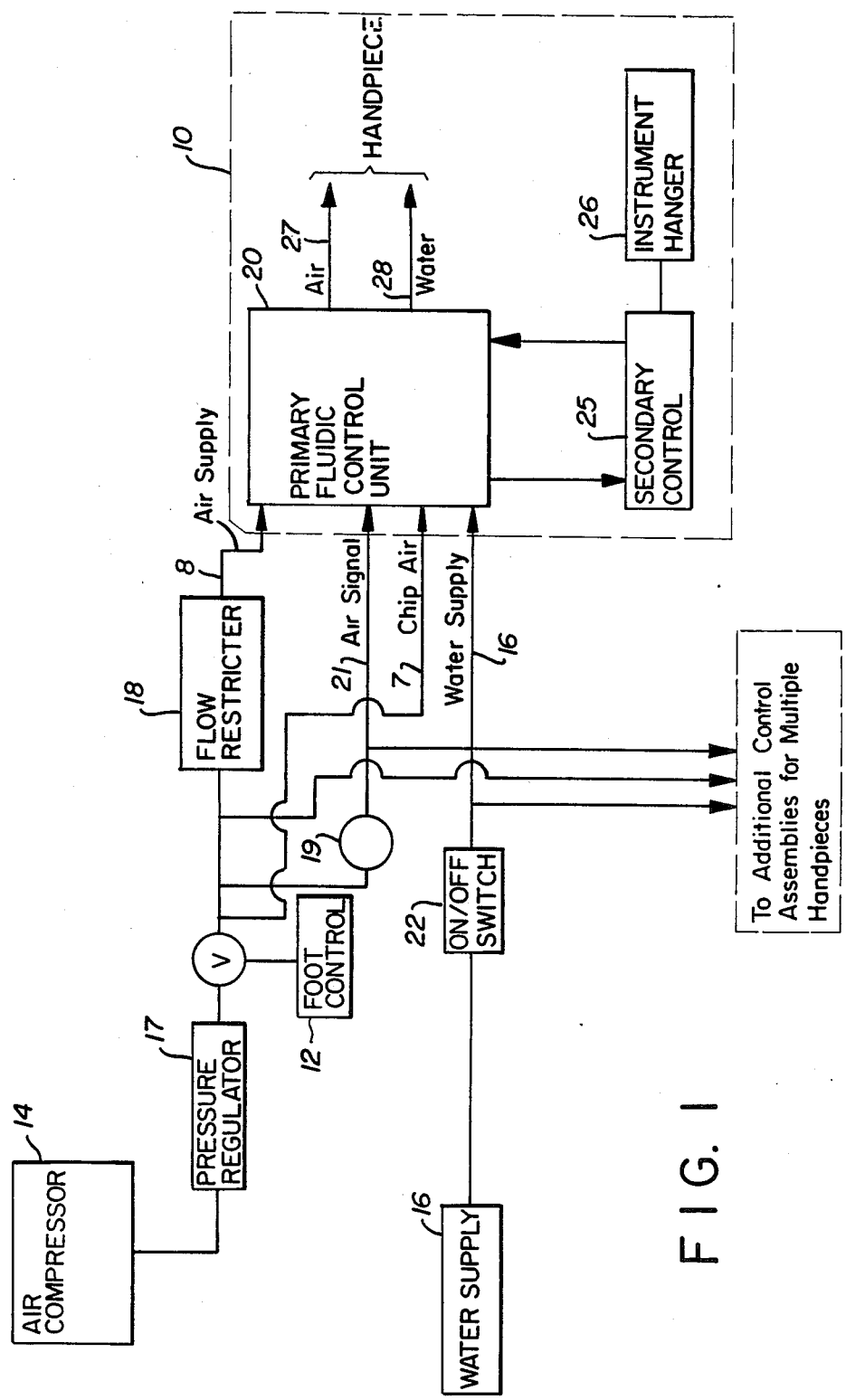
FIG. 1 is a block diagram of a dental handpiece control system incorporating the fluidic control assembly of the present invention.

FIG. 1 shows an overall block diagram of a dental handpiece control system incorporating the fluidic control assembly (10) of the present invention. For multiple handpiece operation, a separate fluidic control assembly (10) is required for each dental handpiece, although the source of compressed air and water may be common to all handpiece controls. Each handpiece control in a multiple handpiece operation may also operate from a common foot switch (12).

A source of compressed air (14) and a source of water (16) is typically available in all dental offices. The source of compressed air (14) is regulated by a pressure regulator (17) and is then fed through a valve (V) and a flow restrictor (18) into an air supply line which feeds into the primary fluidic control unit (20). The flow restrictor (18) is added as an option to provide manually adjustable pressure regulation before delivery to the handpiece. An adjustable pinch valve may be used for the flow restrictor (18). The valve (V) is conventional and operated by the foot switch (12). The regulated compressed air through valve (V) is also fed through an air-operated switch (19) in line (21). The air-operated switch (19) may be manually operated or responsive to the foot switch (14) to provide an additional air signal to the control unit (20). Water is supplied to the unit (20) from the water supply (16) under the control of an on/off switch (22). The delivery of air and/or water is controlled by the operation of the primary fluidic control (20) in combination with a secondary control (25).

The fluidic control assembly (10) of the present invention comprises the primary fluidic control unit (20) and the secondary control (25). The secondary control (25) preferably forms an integral part of the instrument hanger (26). The instrument hanger (26) represents a conventional cradle for accommodating a dental tool or handpiece (H), such as a dental drill.

The primary fluidic control unit (20) is of modular design and preferably in the form of a miniature-sized cassette which is readily located an mounted in any desired location in the dental office. The control unit (20) may be separated from the secondary control (25) and from the instrument hanger and handpiece. The air and water supply lines (27) and (28) are the only connections from the primary fluidic control unit (20) to the handpiece (H).

Figure 2A:
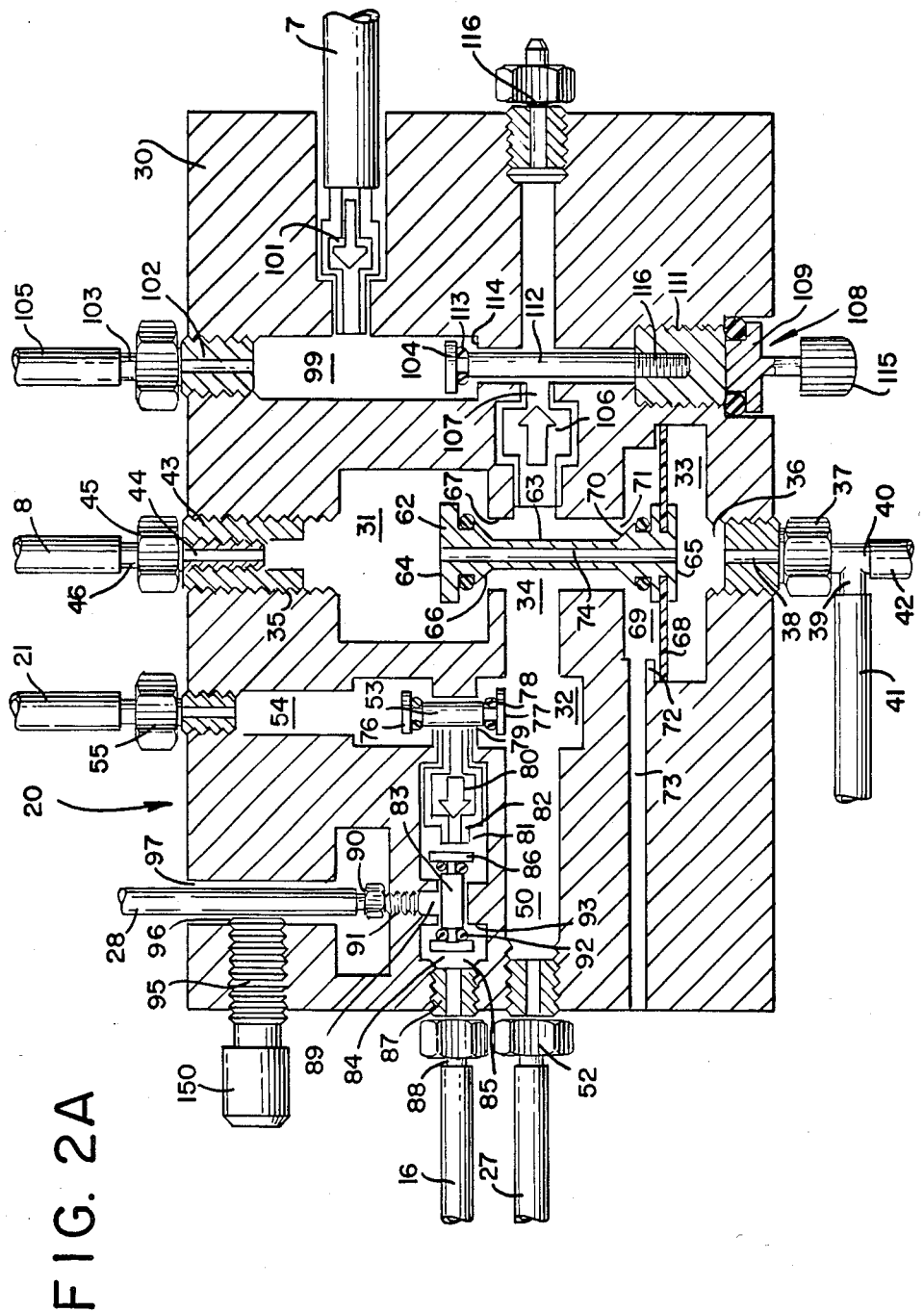
FIG. 2A is a plan view of the primary fluidic control unit of FIG. 1 with its cover plate removed.
Figure 2B:
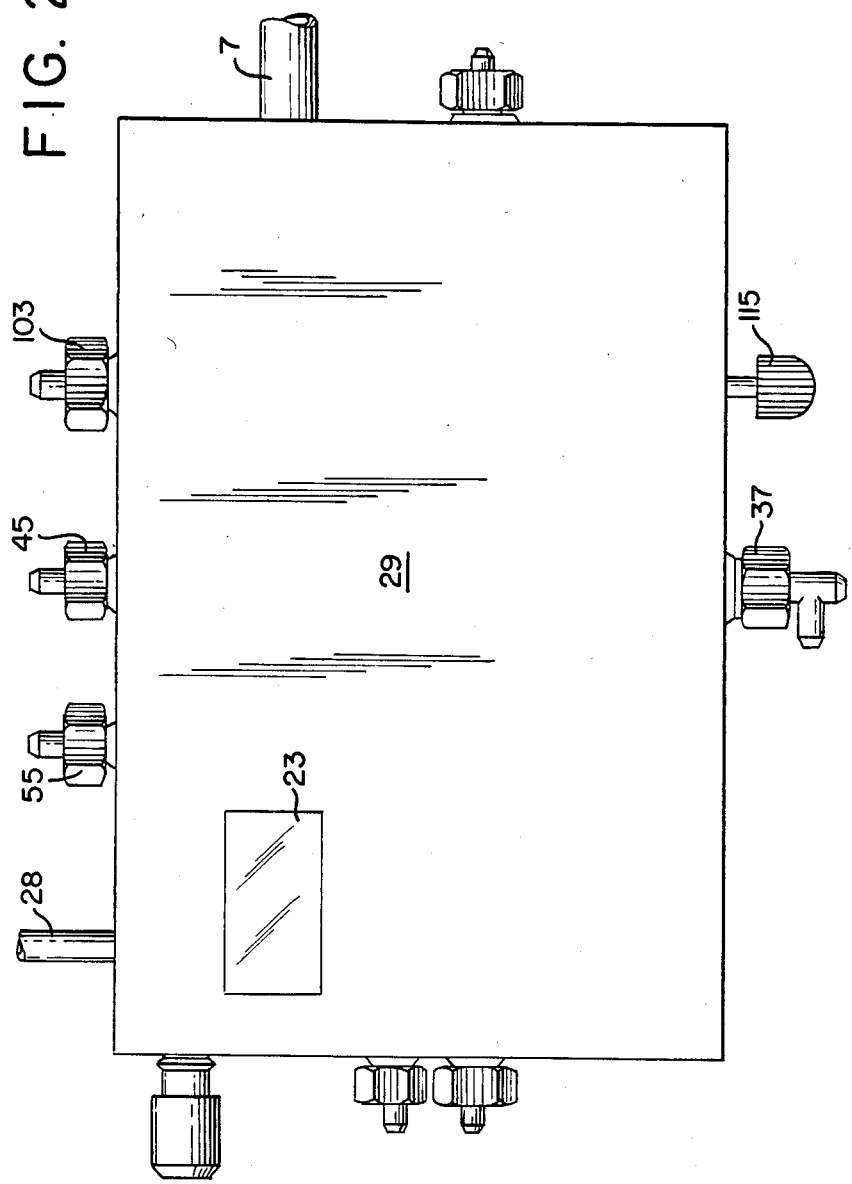
FIG. 2B is a plan view of the primary fluidic control unit of FIG. 2A with the cover plate

The preferred construction of the primary fluidic control unit (20) is shown in FIGS. 2A and 2B. The control unit (20) has a body (30) composed of any desired material, preferably of elastomeric plastic. A plurality of cavities (31), (32) and (33) are molded into the body (30). It is preferred to mold a substantial number of cavities in forming the body (30) so as to minimize the requirement for machining. The exposed cavities are then sealed using a cover plate (29), as is shown in FIG. 2B. The cover plate (29) may have a transparent section (23) forming a window to observe the flow of water through the body (30).

A drilled channel (34) is formed between the cavities (31), (32) and (33), and a plurality of openings (35) and (36) are machined through the body (30) into the open areas (31) and (33), respectively. A threaded fitting (37) is threadably inserted into the opening (36). The fitting (37) includes an open passageway (38) and two barbed connections (39) and (40) extending from the open passageway (38). The primary fluidic control unit (20) is coupled to the secondary control (25) of FIG. 3 through conduits (41) and (42), respectively. Another threaded fitting (43) is threadably inserted into the opening (35). The threaded fitting (43) has a central passageway (44) and a barbed inlet fitting (45), with a central opening (46) forming the main inlet for drive air into the fluidic control unit (20) from the air supply line (8) in FIG. 1.

A channel 50) is formed in the body (30) connecting the area (32) to a barbed outlet fitting 52) for supplying drive air into the tubing (27) under the operation of a main control valve (62). Tubing (27) is connected to the dental handpiece (H). The main control valve (62) includes a drive piston (63) connected between an upper piston head (64) and a lower piston head 65 . The drive piston (63) extends between cavities (31) and (33), with the upper piston head (64) located in cavity 31 and the lower piston head 65) located in cavity 33. The upper piston head (64) has a conical surface (66) for engaging the valve seat (67) to close the control valve (62) when the upper piston head (64) is forced downwardly. The control valve (62) is opened when the lower piston head (65) is urged upwardly, lifting the head (64) off the valve seat (67) to provide ingress to air flow from cavity (31) to area (32) via the channel (34).

A flexible diaphragm (68) is connected to the lower piston head (65) to divide the cavity (33) into sections for forming a separate upper area (69). The lower piston head (65) has a conical surface (70) for engaging a valve seat (71) when the drive piston (63) is urged upwardly to open the main control valve (62). The flexible diaphragm (68) contacts a ledge (72) When the control valve (62) is fully open. In this position the upper section (69) is isolated from the cavity (33). An elongated passageway (73) in the body (30) connects the upper section (69) to the atmosphere to provide fast relief for exhausting pressure from the cassette and to maintain separation between the outlet flow of drive air and the flow of bleed air into area (33).

The drive piston (63) has an orifice (74) extending longitudinally through the piston (63) to provide direct access between cavity (31) and cavity (33). The orifice (74) is a restricted opening of small diameter which permits drive air to bleed through the control valve (62) into cavity (33) at a slow rate. The static pressure in cavity (33) builds up until the control valve (62) is opened. The build up of static pressure is under the control of the secondary control (25) of FIG. 3, as will be explained in greater detail in connection with the description of the operation of the fluidic control unit (20).

A channel (54) is machined in the body (30) for connecting cavity (32) to a hollow inlet fitting (55) to which the air signal line (21) of FIG. 1 is connected. A valve member (53) is interposed in channel (54) to control the flow of water from the inlet conduit (16) to the water supply line (28). The water supply line (28) is connected to the handpiece (H). The valve member (53) has an upper head (76) and a lower head (77). The lower head (77), in conjunction with an "O" ring (78) are urged against a wall surface (79) when drive air is present in channel (50) to open channel (54) permitting air to flow from the air supply line (21) through valve (53) in response to actuation of the air-operated switch (19) in FIG. 1. The air flow through valve (53) is directed into a one-way check valve (80) located in cavity (81). The check valve (80) has a stem (82) and is axially movable within the cavity (81). A two-way valve (83) extends between cavity (81) and cavity (84). The two-way valve (83) has a head (85) in cavity (84) and a head (86) in cavity (81). A hollow fitting (87) with a barbed inlet (88) is connected to the supply of water in the dental office through the inlet tubing (16) for providing water into cavity (84).

When the two-way valve (83) is open, water flows from cavity (84) through a channel (89) into the supply tubing (28) leading to the dental handpiece (H). The supply tubing 28 is connected to a barbed inlet (90) in a hollow fitting (91) threaded into the channel (89). The water pressure in cavity (84) will normally force the head (85) of the two-Way valve (83) to its closed position with the "O" ring (92) engaging the wall surface (93). The two-way valve (83) is forced to open When the stem (82) of the check valve (80) is urged against the head (86) to break the seal formed by the "O" ring (92). The amount of water fed through the tubing (28) is controlled by a pinch valve (95) represented by an adjustable screw threaded into the body (30) and having one end (96) adapted to contact the supply tube (28) within a channel (97) formed in the body (30).

The body (30) of the control unit (20) also includes a channel (99) in Which chip air is directed from the chip air supply line (7) of FIG. 1 through a one-way check valve (101). The chip air is fed through the hollow fitting (102) and barbed inlet (103) into the supply line (105) leading to a separate chip air dispenser (not shown). Supplementary air from the air supply (8) may also be fed into the supply line (105) alone or in combination with the supply of chip air. The supplementary air is supplied through the main control valve (62) when it is open. The drive air from the air supply (8) passes through the open control valve (62) and through a check valve (106) into a channel (107) communicating with channel (99) under the control of a manual air coolant adjustment assembly (108). The air coolant adjustment assembly (108) includes a manually adjustable fitting (109) which has a threaded outer body (110) that is threaded into a female threaded interior opening (111). An elongated piston (112) extends from the body (110) through the channel (107) into the channel (99). The piston (112) has a head (104) at one end with an "O" ring (113) disposed under the head (104). The "O" ring (113) is positioned above a ledge (114). The piston (112) has a male thread (116) at its opposite end which is thread into the body (110). By turning a knurled knob (115) extending from the fitting (109), the piston (112) is forced to turn, moving either upwardly or downwardly in the channel (107). When the "O" ring (113) engages the ledge (114), no supplementary air will flow into the channel (99). The amount of supplementary air is regulated by adjustment of knob (115). An air gauge (not shown) may be connected to a barbed fitting (116) to read the air pressure of the air supply through the check valve (106).

Figure 3:
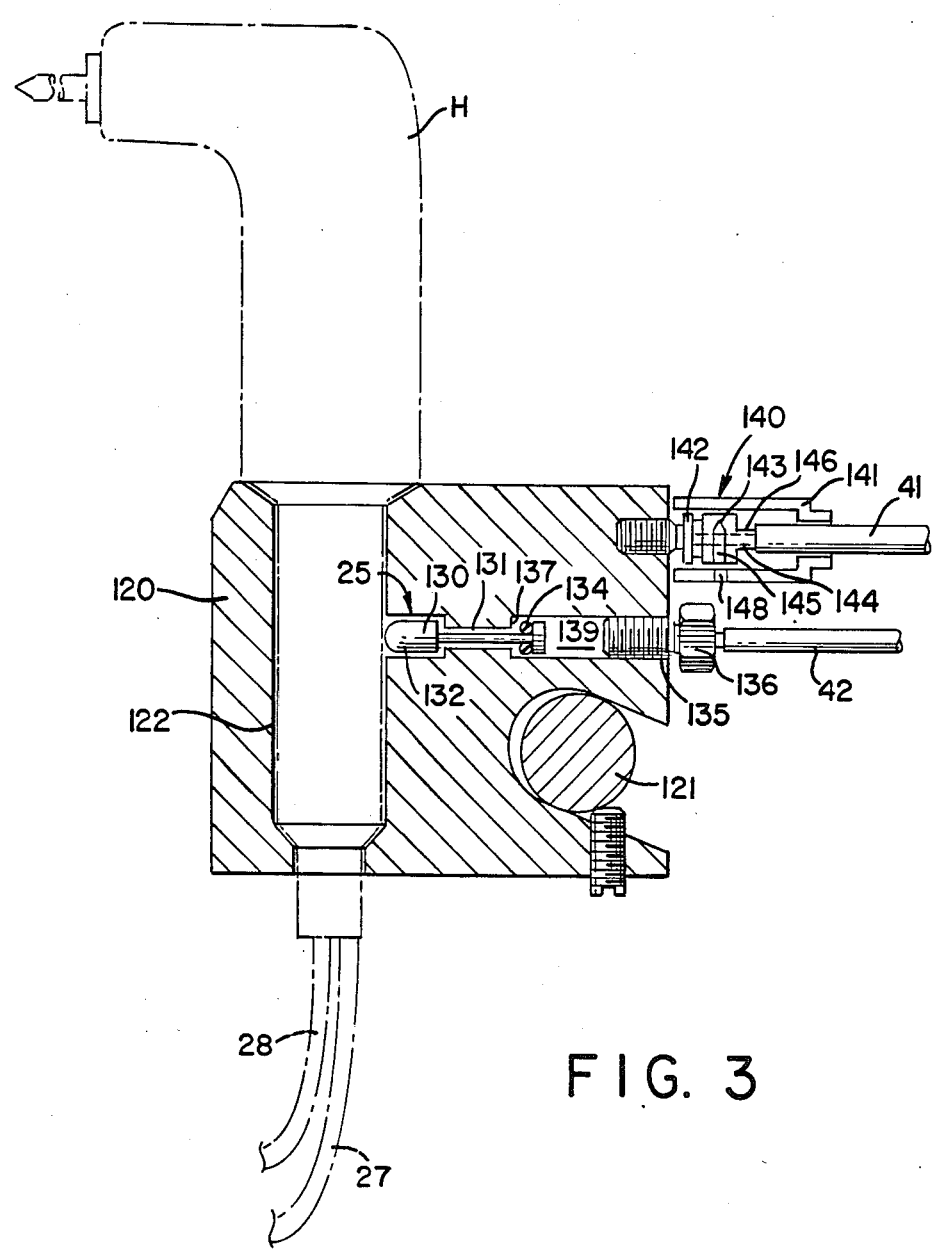
FIG. 3 is a view in cross section of the secondary control in FIG. 1 in combination with an instrument hanger for supporting a dental handpiece.

The secondary control (25), as shown in FIG. 3, is formed as an integral part of the handpiece hanger (120). The hanger (120) is adapted to be mounted in a stationary position affixed to a support (121) which fits into a conventional hanger bracket not shown) in the dental office. The handpiece (H), shown in phantom lines, rests in the cavity (122) of the hanger (120). In the at-rest position, the handpiece (H) presses against the secondary control valve (130) which lies in a channel (131) formed in the hanger (120). The forward end (132) of the control valve (130) is movable laterally over a relatively small distance. The control valve (130) has a head (133) at its opposite end with an "O" ring (134) mounted thereabout. A hollow fitting (135) with a barbed inlet (136) is threadably inserted into the cavity (137). The tubular conduit (42) is connected to the barbed inlet (136) for coupling the cavity (137) in hanger (120) to the cavity (33) in the control unit (20).

A rotary valve assembly (140) is also connected to the hanger (120) to enable a dental burr to be changed in the dental drill without operation of the drill. The rotary valve assembly (140) has a tubular body (141) which is rotatably mounted over a fitting (142) threaded into the hanger (120). A valve (143) is connected to the fitting (142). The valve (143) has a central opening (144) and a cross drilling (145). The tube (41) is mounted over an inlet (146) to provide direct access between the cavity (33) in the control unit (20) and the opening (144). The tubular body (141) of the rotary valve assembly (140) has an aperture (148) which is manually alignable with the cross drilling (145) upon rotation of the body (141). in the aligned or open position, the rotary valve assembly, (140) permits removal of a burr without operation of the dental turbine. In the closed position, with the opening (148) out of alignment with cross drilling (145), the secondary control (25) determines if air and Water is supplied to the handpiece (H).

OPERATION OF THE FLUIDIC CONTROL

With the handpiece (H) at rest in the hanger (120), the secondary control valve (132) is physically shifted to its open position with the head (133) and "O38 ring (134) displaced from the ledge (137). In this position, air is permitted to escape into the atmosphere through the cavity (122). The discharged flow of air is so low, however, that it cannot be heard. The air escapes from around the forward end (132) of the control valve (130). The escape of air from the secondary control valve (132) prevents any build-up of pressure in cavity (33) of the control unit (20). Accordingly, the drive air flowing into chamber (31) from the air supply line (8) will keep the main control valve (62) closed. Upon removal of the dental handpiece (H) from the hanger (120), the air flow through conduit (42) will force the secondary control valve (130) to close. Assuming the rotary valve assembly (140) is in the closed position, with the valve (143) out of alignment with aperture (148), a back pressure Will develop in cavity (33) increasing the static pressure until a predetermined pressure is reached, sufficient to open the main control valve (62) by forcing the diaphragm member (68) upwards. This occurs relatively rapidly, opening the main supply of drive air from cavity (31) through the open control valve (62), through channel (50) and into the air supply line (27) to operate the drill.

If a supply of water to the drill is also desired, the air switch (19) is activated under the operation of the foot control or manually to provide a supply of air through line (21). This depresses the valve member 53), which allows drive air from cavity (32) to enter check valve (80), moving it axially into contact with the head (86) of the two-way valve (83) which, in turn, opens valve (83) to permit water to pass from supply line (16) into the supply conduit 28). The flow of water is controlled by the flow control pinch valve (95) under the manual operation of knob (150).

If the handpiece (H) is momentarily returned to the hanger (120), drive air immediately ceases to flow as a result of closing the main control valve (62) by releasing the static pressure in cavity (33). A burr can be changed in the dental drill without the supply of drive air to the drill by unlocking the rotary valve assembly (140). This permits air to escape from the aperture (148) and prevents any build-up of pressure in cavity (33).

Although only one handpiece control unit (20) is shown for a single handpiece (H), if multiple handpieces are to be controlled, a corresponding multiple number of control units (20) are necessary. The multiple control units (20) may be arranged in tandem using the said source of air and water, as shown in FIG. 1.

What I claim is:

1. A fluidic control assembly for controlling the supply of drive air and/or water from respective sources of supply to a tool adapted to be removably stored in a hanger including a primary fluidic control unit and a secondary control, wherein said primary control unit is formed from a modular body comprising:
   a primary control chamber having a main inlet and a main outlet, with said main outlet coupled to said tool:
   means for directing drive air into said control chamber from said main inlet;
   a control valve for controlling the flow of drive air from said control chamber to said main outlet;
   a secondary chamber;
   means for bleeding air from said control chamber into said secondary chamber;
   means in said secondary chamber for operating said control valve in response to a predetermined pressure level in said secondary chamber; and
   means for discharging air from said secondary chamber into said secondary control with said secondary control including means for blocking the discharge of air from said secondary chamber in response to the absence of said tool from said hanger.

2. A fluidic control assembly, as defined in claim 1, wherein said secondary control comprises a valve having a first position responsive to the presence of said tool in said hanger for discharging air from said secondary chamber into the atmosphere, and a second position responsive to the absence of said tool for blocking air from said secondary chamber to cause a build-up of pressure in said secondary chamber.

3. A fluidic control assembly, as defined in claim 2, Wherein said secondary control valve is located in the hanger for said tool at a location adapted to make physical contact with said tool when said tool is present and wherein said secondary control valve is slidably movable in response to the presence and absence of said tool.

4. A fluidic control assembly, as defined in claim 2, wherein said means in said secondary chamber comprises a diaphragm connected to said control valve and being responsive to the pressure in said secondary chamber above a predetermined level for moving said control valve into an open position.

5. A fluidic control assembly, as defined in claim 4, further comprising manually operated means coupled to said secondary chamber and having an adjustable position for providing a secondary opening for discharging air from the secondary chamber independent of the location of the tool.

6. A fluidic control assembly, as defined in claim 5, further comprising means in said primary control for controlling the flow of water from the water supply to said tool in response to the flow of drive air through said main outlet.

7. A fluidic control assembly, as defined in claim 6, wherein said means comprises a movable two-way valve With a first valve head at one end responsive to the pressure from the water supply for closing said valve, and a second valve head at the opposite end and means responsive to the presence of said drive air for moving said second valve head to open said valve.

8. A fluidic control assembly, as defined in claim 7, further comprising manual pinch valve means for restricting the flow of water to said tool.

* * * * *